United States Patent
Anderson

(10) Patent No.: US 9,357,760 B2
(45) Date of Patent: Jun. 7, 2016

(54) NETWORKED CHEMICAL DISPERSION SYSTEM

(75) Inventor: Noel Wayne Anderson, Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 865 days.

(21) Appl. No.: 13/398,109

(22) Filed: Feb. 16, 2012

(65) Prior Publication Data
US 2012/0150355 A1 Jun. 14, 2012

Related U.S. Application Data

(62) Division of application No. 12/860,036, filed on Aug. 20, 2010.

(51) Int. Cl.
*A61L 101/00* (2006.01)
*A01M 1/20* (2006.01)

(52) U.S. Cl.
CPC .......... *A01M 1/2022* (2013.01); *A61L 2209/11* (2013.01); *A61L 2209/111* (2013.01); *A61L 2209/13* (2013.01)

(58) Field of Classification Search
CPC ... A01M 1/2022; A61L 2209/13; G05D 7/06; G05D 3/20; G06N 5/00
See application file for complete search history.

(56) References Cited

U.S. PATENT DOCUMENTS

| | | |
|---|---|---|
| 3,674,652 A | 7/1972 | Brown |
| 3,931,413 A | 1/1976 | Frick et al. |
| 4,067,714 A | 1/1978 | Willard, Sr. |
| 4,083,494 A | 4/1978 | Ballu |
| 4,146,383 A | 3/1979 | Hanway et al. |
| 4,150,970 A | 4/1979 | Ries et al. |
| 4,175,394 A | 11/1979 | Wiesboeck |
| 4,286,530 A | 9/1981 | Conley |
| 4,315,599 A | 2/1982 | Biancardi |
| 4,342,176 A | 8/1982 | Wolfe |
| 4,358,054 A | 11/1982 | Ehrat |
| 4,385,500 A | 5/1983 | Kjelgaard et al. |
| 4,398,384 A | 8/1983 | Klinner |
| 4,433,552 A | 2/1984 | Smith |
| 4,516,723 A | 5/1985 | Hesse |
| 4,588,127 A | 5/1986 | Ehrat |
| 4,610,122 A | 9/1986 | De Clercq |
| 4,638,594 A | 1/1987 | Huguet et al. |
| 4,704,986 A | 11/1987 | Remp et al. |

(Continued)

FOREIGN PATENT DOCUMENTS

| | | |
|---|---|---|
| DE | 3830647 A1 | 3/1990 |
| DE | 4413739 A1 | 10/1995 |

(Continued)

OTHER PUBLICATIONS

"The AW-5000-MC," Air Water Corporation, http://www.airwatercorp.com, Feb. 12, 2010, 1 page.

(Continued)

*Primary Examiner* — Lyle Alexander
(74) *Attorney, Agent, or Firm* — Yee & Associates, P.C.

(57) ABSTRACT

The illustrative embodiments provide a chemical dispersion system comprising a number of chemical dispersion nodes, a chemical dispersion manager, and a processor unit. The processor unit executes the chemical dispersion manager to identify a pest problem and generate a chemical dispersion plan for execution by the number of chemical dispersion nodes.

8 Claims, 6 Drawing Sheets

(56) References Cited

U.S. PATENT DOCUMENTS

| | | |
|---|---|---|
| 4,757,688 A | 7/1988 | Basiulis et al. |
| 4,832,263 A | 5/1989 | Poynor |
| 4,871,447 A | 10/1989 | Adamache |
| 4,903,903 A | 2/1990 | Benen |
| 4,949,656 A | 8/1990 | Lyle et al. |
| 4,970,973 A | 11/1990 | Lyle et al. |
| 4,982,898 A | 1/1991 | Ballu |
| 4,992,942 A | 2/1991 | Bauerle et al. |
| 5,076,497 A | 12/1991 | Rabitsch |
| 5,092,343 A | 3/1992 | Spitzer et al. |
| 5,092,422 A | 3/1992 | Hood, Jr. et al. |
| 5,140,917 A | 8/1992 | Swanson |
| 5,248,090 A | 9/1993 | Williamson |
| 5,255,857 A | 10/1993 | Hunt |
| 5,355,815 A | 10/1994 | Monson |
| 5,442,552 A | 8/1995 | Slaughter et al. |
| 5,601,236 A | 2/1997 | Wold |
| 5,740,038 A | 4/1998 | Hergert |
| 5,840,102 A | 11/1998 | McCracken |
| 5,870,302 A | 2/1999 | Oliver |
| 5,884,224 A | 3/1999 | McNabb et al. |
| 5,907,925 A | 6/1999 | Guyot |
| 5,913,915 A | 6/1999 | McQuinn |
| 5,915,313 A | 6/1999 | Bender et al. |
| 5,919,242 A | 7/1999 | Greatline et al. |
| 5,924,371 A | 7/1999 | Flamme et al. |
| 5,927,603 A | 7/1999 | McNabb |
| 5,979,703 A | 11/1999 | Nystrom |
| 5,991,687 A | 11/1999 | Hale et al. |
| 5,995,895 A | 11/1999 | Watt et al. |
| 6,039,212 A | 3/2000 | Singh |
| 6,079,340 A | 6/2000 | Flamme et al. |
| 6,089,743 A | 7/2000 | McQuinn |
| 6,116,519 A | 9/2000 | Williamson |
| 6,122,581 A | 9/2000 | McQuinn |
| 6,129,520 A | 10/2000 | Cooper |
| 6,141,614 A | 10/2000 | Janzen et al. |
| 6,178,253 B1 | 1/2001 | Hendrickson et al. |
| 6,199,000 B1 | 3/2001 | Keller et al. |
| 6,230,091 B1 | 5/2001 | McQuinn |
| 6,337,971 B1 | 1/2002 | Abts |
| 6,443,365 B1 | 9/2002 | Tucker et al. |
| 6,510,367 B1 | 1/2003 | McQuinn |
| 6,516,271 B2 | 2/2003 | Upadhyaya et al. |
| 6,549,851 B2 | 4/2003 | Greensides |
| 6,553,299 B1 | 4/2003 | Keller et al. |
| 6,574,979 B2 | 6/2003 | Faqih |
| 6,596,996 B1 | 7/2003 | Stone et al. |
| 6,597,991 B1 | 7/2003 | Meron et al. |
| 6,616,374 B2 | 9/2003 | Starr |
| 6,666,384 B2 | 12/2003 | Prandi |
| 6,671,698 B2 | 12/2003 | Pickett et al. |
| 6,684,648 B2 | 2/2004 | Faqih |
| 6,691,135 B2 | 2/2004 | Wagner et al. |
| 6,755,362 B2 | 6/2004 | Krieger et al. |
| 6,778,887 B2 * | 8/2004 | Britton ............ 701/21 |
| 6,792,395 B2 | 9/2004 | Roberts |
| 6,802,153 B2 | 10/2004 | DuBois et al. |
| 6,854,209 B2 | 2/2005 | Van Horssen et al. |
| 6,862,083 B1 | 3/2005 | McConnell, Sr. et al. |
| 6,877,325 B1 | 4/2005 | Lawless |
| 6,907,319 B2 | 6/2005 | Hoelscher et al. |
| 6,928,339 B2 | 8/2005 | Barker |
| 6,941,225 B2 | 9/2005 | Upadhyaya et al. |
| 6,963,881 B2 | 11/2005 | Pickett et al. |
| 6,975,245 B1 | 12/2005 | Slater et al. |
| 6,978,794 B2 | 12/2005 | Dukes et al. |
| 7,063,276 B2 | 6/2006 | Newton |
| 7,069,692 B2 | 7/2006 | Kuiper et al. |
| 7,089,763 B2 | 8/2006 | Forsberg et al. |
| 7,171,912 B2 | 2/2007 | Fraisse et al. |
| 7,182,274 B2 | 2/2007 | Nies |
| 7,182,445 B2 | 2/2007 | Johnson et al. |
| 7,275,042 B1 | 9/2007 | Kelly et al. |
| 7,280,892 B2 | 10/2007 | Bavel |
| 7,317,972 B2 | 1/2008 | Addink et al. |
| 7,343,262 B2 | 3/2008 | Baumgarten et al. |
| 7,408,145 B2 | 8/2008 | Holland |
| 7,455,245 B2 | 11/2008 | Sipinski et al. |
| 7,469,707 B2 | 12/2008 | Anderson et al. |
| 7,565,139 B2 | 7/2009 | Neven, Sr. et al. |
| 7,577,105 B2 | 8/2009 | Takeyoshi et al. |
| 7,610,122 B2 | 10/2009 | Anderson |
| 7,617,992 B2 | 11/2009 | Ivans |
| 7,686,499 B2 | 3/2010 | Dykstra et al. |
| 7,775,168 B2 | 8/2010 | Sidhwa et al. |
| 7,805,221 B2 | 9/2010 | Nickerson |
| 7,809,475 B2 | 10/2010 | Kaprielian |
| 7,837,958 B2 | 11/2010 | Crapser et al. |
| 7,844,368 B2 | 11/2010 | Alexanian |
| 7,854,108 B2 | 12/2010 | Koselka et al. |
| 7,930,085 B2 | 4/2011 | Anderson et al. |
| 7,957,850 B2 | 6/2011 | Anderson |
| 8,028,470 B2 | 10/2011 | Anderson |
| 8,150,554 B2 | 4/2012 | Anderson |
| 8,170,405 B2 | 5/2012 | Harris |
| 2002/0011075 A1 | 1/2002 | Faqih |
| 2002/0170229 A1 | 11/2002 | Ton et al. |
| 2003/0019408 A1 | 1/2003 | Fraisse et al. |
| 2003/0215354 A1 | 11/2003 | Clark et al. |
| 2003/0229434 A1 | 12/2003 | Miedema |
| 2004/0034459 A1 | 2/2004 | Hoelscher et al. |
| 2004/0078092 A1 | 4/2004 | Addink et al. |
| 2004/0231240 A1 | 11/2004 | Kuiper et al. |
| 2005/0129034 A1 | 6/2005 | Takeyoshi et al. |
| 2005/0187665 A1 | 8/2005 | Fu |
| 2005/0199842 A1 | 9/2005 | Parsons et al. |
| 2006/0026556 A1 | 2/2006 | Nishimura |
| 2006/0089260 A1 | 4/2006 | Di et al. |
| 2007/0042803 A1 | 2/2007 | Anderson |
| 2007/0220808 A1 | 9/2007 | Kaprielian et al. |
| 2008/0061163 A1 | 3/2008 | Kubby et al. |
| 2008/0097653 A1 | 4/2008 | Kaprielian et al. |
| 2008/0190020 A1 | 8/2008 | Todd |
| 2008/0288116 A1 | 11/2008 | Nickerson |
| 2009/0001193 A1 | 1/2009 | Parsons et al. |
| 2009/0019826 A1 | 1/2009 | Rigney |
| 2009/0179165 A1 | 7/2009 | Parsons et al. |
| 2009/0241580 A1 | 10/2009 | Hill et al. |
| 2009/0259483 A1 | 10/2009 | Hendrickson et al. |
| 2009/0281672 A1 | 11/2009 | Pourzia |
| 2009/0314862 A1 | 12/2009 | Bauman et al. |
| 2010/0032495 A1 | 2/2010 | Abts |
| 2010/0034466 A1 | 2/2010 | Jing et al. |
| 2010/0054543 A1 | 3/2010 | Pachys |
| 2010/0109946 A1 | 5/2010 | Pande |
| 2010/0243754 A1 | 9/2010 | Harris |
| 2010/0263275 A1 | 10/2010 | Anderson |
| 2010/0268390 A1 | 10/2010 | Anderson |
| 2010/0268391 A1 | 10/2010 | Anderson |
| 2010/0268562 A1 | 10/2010 | Anderson |
| 2010/0268679 A1 | 10/2010 | Anderson |
| 2010/0313799 A1 | 12/2010 | Sidhwa et al. |
| 2010/0332475 A1 | 12/2010 | Birdwell et al. |
| 2011/0089260 A1 | 4/2011 | Van Roemburg |
| 2011/0301755 A1 | 12/2011 | Anderson |
| 2011/0313577 A1 | 12/2011 | Anderson |
| 2012/0042563 A1 | 2/2012 | Anderson |
| 2012/0046790 A1 | 2/2012 | Anderson |
| 2012/0046837 A1 | 2/2012 | Anderson |

FOREIGN PATENT DOCUMENTS

| | | |
|---|---|---|
| DE | 10002880 C1 | 6/2001 |
| DE | 10148747 A1 | 4/2003 |
| DE | 10221948 A1 | 11/2003 |
| EP | 2243353 A1 | 10/2010 |
| EP | 2423860 A2 | 2/2012 |
| EP | 2426628 A2 | 3/2012 |
| GB | 1597988 | 9/1981 |
| GB | 1603661 | 11/1981 |
| GB | 2462720 A | 2/2010 |

(56) References Cited

FOREIGN PATENT DOCUMENTS

| WO | 0232222 A1 | 4/2002 |
| WO | 2006060854 A1 | 6/2006 |
| WO | 2009059373 A1 | 5/2009 |

OTHER PUBLICATIONS

Chesmore, "The Automated Identification of Taxa: Concepts and Applications," In: Automated Taxon Identification Systematics: Theory, Approaches and Applications, McLeod (Ed.), CRC Press, Boca Raton, Florida, pp. 83-100, Jul. 23, 2007.

El-Helly et al., "Integrating Diagnostic Expert System with Image Processing via Loosely Coupled Technique," INFOS2004, The 2nd International Conference on Informatics and Systems, Cairo, Egypt, Mar. 6-8, 2004, 15 pages.

Fleurat-Lessard et al., "Acoustic Detection and Automatic Identification of Insect Stages Activity in Grain Bulks by Noise Spectra Processing Through Classification Algorithms," 9th International Working Conference on Stored Product Protection, Sao Paulo, Brazil, Oct. 15-18, 2006, 11 pages.

Fynn, "A Decision Model for Resource Management Using Rule-Based Utility Functions and Parameter Selection," Dissertation, Ohio State University, Columbus, Ohio, 1988, 209 pages.

Garcia, "Eavesdropping on Insects in Soil and Plants," U.S. Department of Agriculture, Agricultural Research Service, Jan. 5, 2001, (last modified Jul. 10, 2012), 1 page.

Griepentrog et al., "Autonomous Systems for Plant Protection," In: Precision Crop Protection—The Challenge and Use of Heterogeneity, Oerke et al. (Eds.), Springer Netherlands, New York, New York, pp. 323-333, Aug. 2010.

Gwatipedza et al., "A General Monopolistic Competition Economic Model of the Horticultural Industry with a Risk of Invasion," U.S. Department of Agriculture, Dec. 6, 2007, 27 pages.

Hardaker et al., "Assessment of the Output of a Stochastic Decision Model," Australian Journal of Agricultural Economics, 17(3):170-178, Dec. 1973.

Munoz-Carpena et al., "Automatic Irrigation Based on Soil Moisture for Vegetable Crops," University of Florida, Gainesville, Florida, IFAS Extension, No. ABE356, pp. 1-5, Jun. 2005.

Muselli et al., "Dew Water Collector for Potable Water in Ajaccio (Corsica Island, France)," Atmospheric Research, 64:297-312, 2002.

Pande et al., "mKRISHI: A Mobile Multimedia Agro Advisory System for Remote Rural Farmers," http://www.ics.uci.edu/jain/papers/ACM_mm09_mKRISHI_non_blind.pdf, Apr. 20, 2009, 12 pages.

Perret et al., "Humidification-Dehumidification System in a Greenhouse for Sustainable Crop Production," 9th International Water Technology Conference, IWTC9 2005, Sharm El-Sheikh, Egypt, Biosystems Engineering, Academic Press, 91(3):849-862, Jul. 2005.

Pontikakos et al., "Location-Aware System for Olive Fruit Fly Spray Control," Computers and Electronics in Agriculture, 70:355-368, 2010.

Potamitis et al., "On Automatic Bioacoustic Detection of Pests: The Cases of Rhynchophorus ferrugineus and Sitophilus oryzae," Journal of Economic Entomology, 102(4):1681-1690, Aug. 2009.

Prasad et al., "A Study on Various Expert Systems in Agriculture," Georgian Electronic Scientific Jounal: Computer Science and Telecommunications, 4(11):81-86, Nov. 2006.

Romero, "Rish Programming for Agricultural Resource Allocation: A Multidimensional Risk Approach," Annals of Operations Research, 94:57-68, Jan. 2000.

Sim et al., "Implementation of an XML-based Multimedia Pests Information System for USN Environment," Proceedings of the 10th ACIS International Conference on Software Engineering, Artificial Intelligences, Networking and Parallel/Distributed Computing, pp. 597-601, May 27, 2009.

Tomasini, "Insect (Adult and Larva) Detection Equipment in Stored Grain—EWD Technology," EWD Training Seminar Lite, Saint-ChamaslCarqueiranne, France, May 10-11, 2004, 8 pages.

Woodford, "Connectionist-Based Intelligent Information Systems for Image Analysis and Knowledge Engineering: Applications in Horticulture," Thesis, The University of Otago, Dunedin, New Zealand, pp. 1-9, Dec. 11, 2003.

European Search Report regarding European Application No. 10160613.5, dated Jul. 26, 2010, 6 pages.

European Office Action regarding European Application No. 10160613.5, dated Mar. 29, 2012, 4 pages.

European Search Report regarding European Application No. 10160618.4, dated Jul. 26, 2010, 5 pages.

European Search Report regarding European Application No. 11170005.0, dated Oct. 25, 2011, 8 pages.

European Search Report regarding European Application No. 11176681.2, dated Jun. 6, 2012, 8 pages.

European Search Report regarding European Application No. 11176689.5, dated Jun. 14, 2012, 10 pages.

European Search Report regarding European Application No. 11176697.8, dated Dec. 22, 2011, 7 pages.

Eisenberg, "Digital Field Guides Eliminate the Guesswork," The New York Times, May 10, 2009, 2 pages.

"Google Goggles (Labs): Overview," http://google.com/support/mobile/ . . . /answer.p . . ., Jun. 1, 2010, 2 pages.

Schwartz, "Engineer Uses Solar Energy, Wax, and Human Sweat to Fight Malaria," http://cleantechnica.com/2009/01/31/engineer-uses-solar-energy-wax-and-human-sweat-to-fight-malaria/, Jan. 31, 2009, 3 pages.

"Google Goggles," YouTube, www.youtube.com/watch?v=Hh, accessed Jul. 19, 2010, 2 pages.

\* cited by examiner

NETWORKED CHEMICAL DISPERSION SYSTEM

CLAIM OF PRIORITY

This application is a divisional of and claims the benefit of priority to U.S. patent application Ser. No. 12/860,036, filed on Aug. 20, 2010 and entitled "Networked Chemical Dispersion System", status pending. Incorporation is made herein by reference.

CROSS REFERENCE TO RELATED APPLICATIONS

This application is related to commonly assigned and co-pending U.S. patent application Ser. No. 12/859,913 filed on Aug. 20, 2010 and entitled "Robotic Pesticide Application"; U.S. patent application Ser. No. 12/859,877 filed on Aug. 20, 2010 and entitled "Automated Plant Problem Resolution" all of which are hereby incorporated by reference.

FIELD OF THE INVENTION

The present invention relates generally to a pest control system and, more particularly, to a networked chemical dispersion system.

BACKGROUND OF THE INVENTION

Pests and insects can present undesirable conditions both indoors and outdoors that may affect plants, animals, and humans. These pests and insects may have varied affect on different types of plants, animals, and humans, for example. Different climates and regions may also present varied types of pests and insects to manage.

Various chemicals are used to manage pests and insects in both indoor and outdoor settings. These chemicals may present a number of additional considerations, such as the environmental effect, effectiveness, endurance, frequency of re-application, as well as the affect on living things, such as animals, humans, and plants.

SUMMARY

The different illustrative embodiments provide a chemical dispersion system comprising a number of chemical dispersion nodes, a chemical dispersion manager, and a processor unit. The processor unit executes the chemical dispersion manager in response to a pest problem to generate a chemical dispersion plan for execution by the number of chemical dispersion nodes.

The different illustrative embodiments further provide a method for networked chemical dispersion. A user selection of an area for chemical treatment is received. Information associated with the area and the user selection is identified. A chemical dispersion plan is generated using the information identified. The chemical dispersion plan is transmitted to a number of chemical dispersion nodes.

The different illustrative embodiments further provide an apparatus for chemical dispersion comprising a processor unit, a number of sensors, a power source, and a cartridge. The processor unit is configured to receive chemical dispersion plans. The power source is configured to provide power to the processor unit and the number of sensors. The cartridge is configured to execute the chemical dispersion plans responsive to a trigger from the processor unit.

The different illustrative embodiments further provide a method for executing a chemical dispersion plan. A processor unit receives a chemical dispersion plan from a remote location using a communications unit. An amount of a chemical to disperse is identified using the chemical dispersion plan. A time for dispersion of the chemical is identified using the chemical dispersion plan. A cartridge is triggered to disperse the amount identified of the chemical at the time identified.

The features, functions, and advantages can be achieved independently in various embodiments of the present invention or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and advantages thereof, will best be understood by reference to the following detailed description of an illustrative embodiment of the present invention when read in conjunction with the accompanying drawings, wherein:

DESCRIPTION OF THE PREFERRED EMBODIMENT

Figure 1:
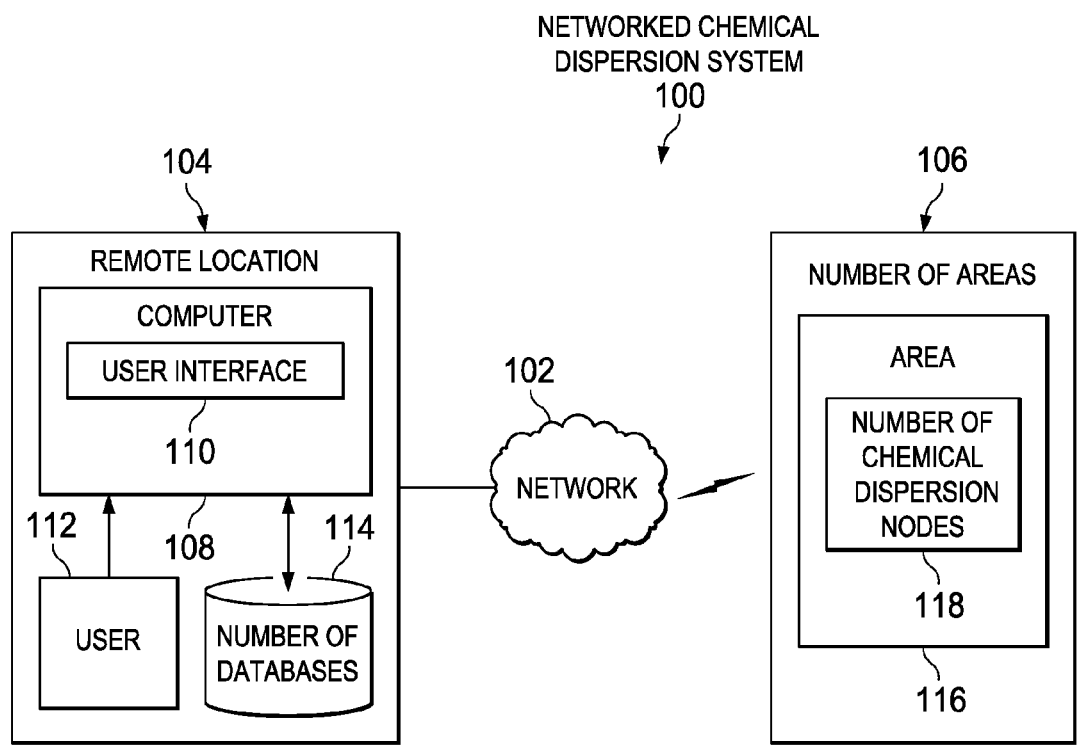
FIG. 1 is a block diagram of a networked chemical dispersion system in which an illustrative embodiment may be implemented.

FIG. 1 is a block diagram of a networked chemical dispersion system in which an illustrative embodiment may be implemented. Networked chemical dispersion system 100 may be implemented in a network of computers in which the illustrative embodiments may be implemented. Networked chemical dispersion system 100 contains network 102, which is the medium used to provide communications links between various devices and computers connected together within networked chemical dispersion system 100, such as remote location 104 and number of chemical dispersion nodes 118. Network 102 may include connections, such as wire, wireless communication links, or fiber optic cables.

In the depicted example, remote location 104 connects to network 102 in a hard connection to network 102, while number of chemical dispersion nodes 118 connects to network 102 in a wireless configuration. In another illustrative embodiment, both remote location 104 and number of chemical dispersion nodes 118 may connect to network 102 in a wireless configuration. Remote location 104 may be, for example, personal computers, network computers, smart phones, and/or personal digital assistants. In one illustrative example, remote location 104 provides data, such as boot files, operating system images, and applications, to number of chemical dispersion nodes 118. Number of chemical dispersion nodes 118 is a client to remote location 104 in this example. Networked chemical dispersion system 100 may include additional servers, clients, and other devices not shown.

Networked chemical dispersion system 100 may be used to identify and manage chemical treatment for a number of different pest problems. As used herein, pest problems refers to, for example, without limitation, undesired plants, insects, animals, fungi, single celled organisms, viruses, and/or any other living thing which is unwanted in an area at a given time. Furthermore, as used herein, pest problems refer to airborne or waterborne chemicals or particulates.

Networked chemical dispersion system 100 includes number of areas 106. Number of areas 106 may be, for example, a flowerbed, garden, yard, lawn, landscape, park, agricultural field, athletic field, green, golf course, fairway, rough, orchard, vineyard, or any other area of recreational land. Area 116 may include earth, surface water, and atmosphere sharing the same geo-reference. Area 116 is an illustrative example of one implementation of number of areas 106.

Number of chemical dispersion nodes 118 is implemented in area 116 to manage pest problems for area 116. Number of chemical dispersion nodes 118 may receive information from remote location 104 using network 102.

Remote location 104 includes computer 108, user 112, and number of databases 114. Computer 108 includes user interface 110. User 112 may interact with computer 108 using user interface 110 to provide user input as to which area in number of areas 106 pest management is desired, for example. Computer 108 uses user input and number of databases 114 to identify an area where pest management is desired, identify the pest problem for the area, and generate treatment plans for the pest problems.

The illustration of networked chemical dispersion system 100 in FIG. 1 is intended as an example, and not as an architectural limitation to the manner in which the different illustrative embodiments may be implemented. Other components may be used in addition to or in place of the ones illustrated for networked chemical dispersion system 100 in other illustrative embodiments.

With reference now to FIG. 2, a block diagram of a data processing system is depicted in accordance with an advantageous embodiment. Data processing system 200 is an example of a data processing system that may be used to implement servers and clients, such as remote location 104 and number of chemical dispersion nodes 118 in FIG. 1.

In this illustrative example, data processing system 200 includes communications fabric 202, which provides communications between processor unit 204, memory 206, persistent storage 208, communications unit 210, input/output (I/O) unit 212, and display 214. Processor unit 204 serves to execute instructions for software that may be loaded into memory 206. Processor unit 204 may be a number of processors, a multi-processor core, or some other type of processor, depending on the particular implementation. A number, as used herein with reference to an item, means one or more items. Further, processor unit 204 may be implemented using a number of heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices 216. A storage device is any piece of hardware that is capable of storing information, such as, for example without limitation, data, program code in functional form, and/or other suitable information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard, a mouse, and/or some other suitable input device. Further, input/output unit 212 may send output to a printer. Display 214 provides a mechanism to display information to a user.

Instructions for the operating system, applications and/or programs may be located in storage devices 216, which are in communication with processor unit 204 through communications fabric 202. In these illustrative examples the instruction are in a functional form on persistent storage 208. These instructions may be loaded into memory 206 for execution by processor unit 204. The processes of the different embodiments may be performed by processor unit 204 using computer implemented instructions, which may be located in a memory, such as memory 206.

These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 218 is located in a functional form on computer readable media 220 that is selectively removable and may be loaded onto or transferred to data processing system 200 for execution by processor unit 204. Program code 218 and computer readable media 220 form computer program product 222 in these examples. In one example, computer readable media 220 may be computer readable storage media 224 or computer readable signal media 226. Computer readable storage media 224 may include, for example, an optical or magnetic disk that is inserted or placed into a drive or other device that is part of persistent storage 208 for transfer onto a storage device, such as a hard drive, that is part of persistent storage 208. Computer readable storage media 224 also may take the form of a persistent storage, such as a hard drive, a thumb drive, or a flash memory, that is connected to data processing system 200. In some instances, computer readable storage media 224 may not be removable from data processing system 200. In these illustrative examples, computer readable storage media 224 is a non-transitory computer readable storage medium.

Alternatively, program code 218 may be transferred to data processing system 200 using computer readable signal media 226. Computer readable signal media 226 may be, for example, a propagated data signal containing program code 218. For example, computer readable signal media 226 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 218 may be downloaded over a network to persistent storage 208 from another device or data processing system through computer readable signal media 226 for use within data processing system 200. For instance, program code stored in a computer readable storage medium in a server data processing system may be downloaded over a network from the server to data processing system 200. The data processing system providing program code 218 may be a server computer, a client computer, or some other device capable of storing and transmitting program code 218.

The different components illustrated for data processing system 200 are not meant to provide architectural limitations to the manner in which different embodiments may be implemented. The different advantageous embodiments may be implemented in a data processing system including components in addition to or in place of those illustrated for data processing system 200. Other components shown in FIG. 2 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

As another example, a storage device in data processing system 200 is any hardware apparatus that may store data. Memory 206, persistent storage 208, and computer readable media 220 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206, or a cache such as found in an interface and memory controller hub that may be present in communications fabric 202.

As used herein, the phrase "at least one of", when used with a list of items, means that different combinations of one or more of the items may be used and only one of each item in the list may be needed. For example, "at least one of item A, item B, and item C" may include, for example, without limitation, item A or item A and item B. This example also may include item A, item B, and item C or item B and item C.

As used herein, when a first component is connected to a second component, the first component may be connected to the second component without any additional components. The first component also may be connected to the second component by one or more other components. For example, one electronic device may be connected to another electronic device without any additional electronic devices between the first electronic device and the second electronic device. In some cases, another electronic device may be present between the two electronic devices connected to each other.

The different advantageous embodiments recognize and take into account that identifying and treating problems is currently a labor intensive task. When a pest problem is noticed by a home owner, for example, the home owner typically engages in various manual applications of chemicals to attempt to eradicate the problem. Alternately, the home owner may hire third party to apply chemicals around a yard or home. The home owner must then monitor the results and determine when future applications are necessary. This implementation may involve contacting a professional lawn or gardening service, making a trip to a retailer for supplies, ordering chemicals, studying chemical application, performing the chemical application, cleaning up after the application, and then storing any unused chemicals. This current approach is time consuming and often results in leftover chemicals being stored and presenting potential safety hazards.

The different illustrative embodiments provide a chemical dispersion system comprising a number of chemical dispersion nodes, a chemical dispersion manager, and a processor unit. The processor unit executes the chemical dispersion manager in response to a pest problem to generate a chemical dispersion plan for execution by the number of chemical dispersion nodes.

The different illustrative embodiments further provide a method for networked chemical dispersion. A user selection of an area for chemical treatment is received. Information associated with the area and the user selection is identified. A chemical dispersion plan is generated using the information identified. The chemical dispersion plan is transmitted to a number of chemical dispersion nodes.

The different illustrative embodiments further provide an apparatus for chemical dispersion comprising a processor unit, a number of sensors, a power source, and a cartridge. The processor unit is configured to receive chemical dispersion plans. The power source is configured to provide power to the processor unit and the number of sensors. The cartridge is configured to execute the chemical dispersion plans responsive to a trigger from the processor unit.

The different illustrative embodiments further provide a method for executing a chemical dispersion plan. A processor unit receives a chemical dispersion plan from a remote location using a communications unit. An amount of a chemical to disperse is identified using the chemical dispersion plan. A time for dispersion of the chemical is identified using the chemical dispersion plan. A cartridge is triggered to disperse the amount identified of the chemical at the time identified.

Figure 3:
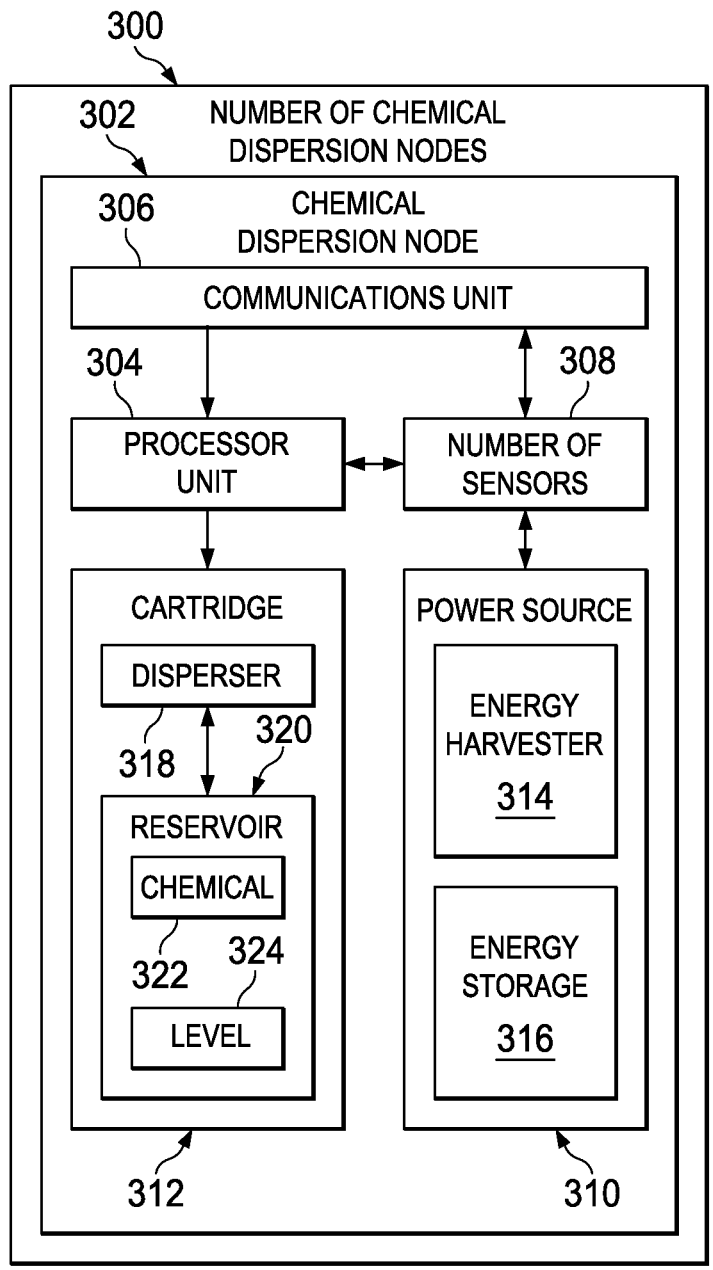
FIG. 3 is a block diagram of a number of chemical dispersion nodes in accordance with an illustrative embodiment.

With reference now to FIG. 3, a block diagram of a number of chemical dispersion nodes is depicted in accordance with an illustrative embodiment. Number of chemical dispersion nodes 300 is an example of one implementation of number of chemical dispersion nodes 118 in FIG. 1.

Chemical dispersion node 302 is an illustrative example of one implementation of number of chemical dispersion nodes 300. Chemical dispersion node 302 includes processor unit 304, communications unit 306, number of sensors 308, power source 310, and cartridge 312.

Figure 2:
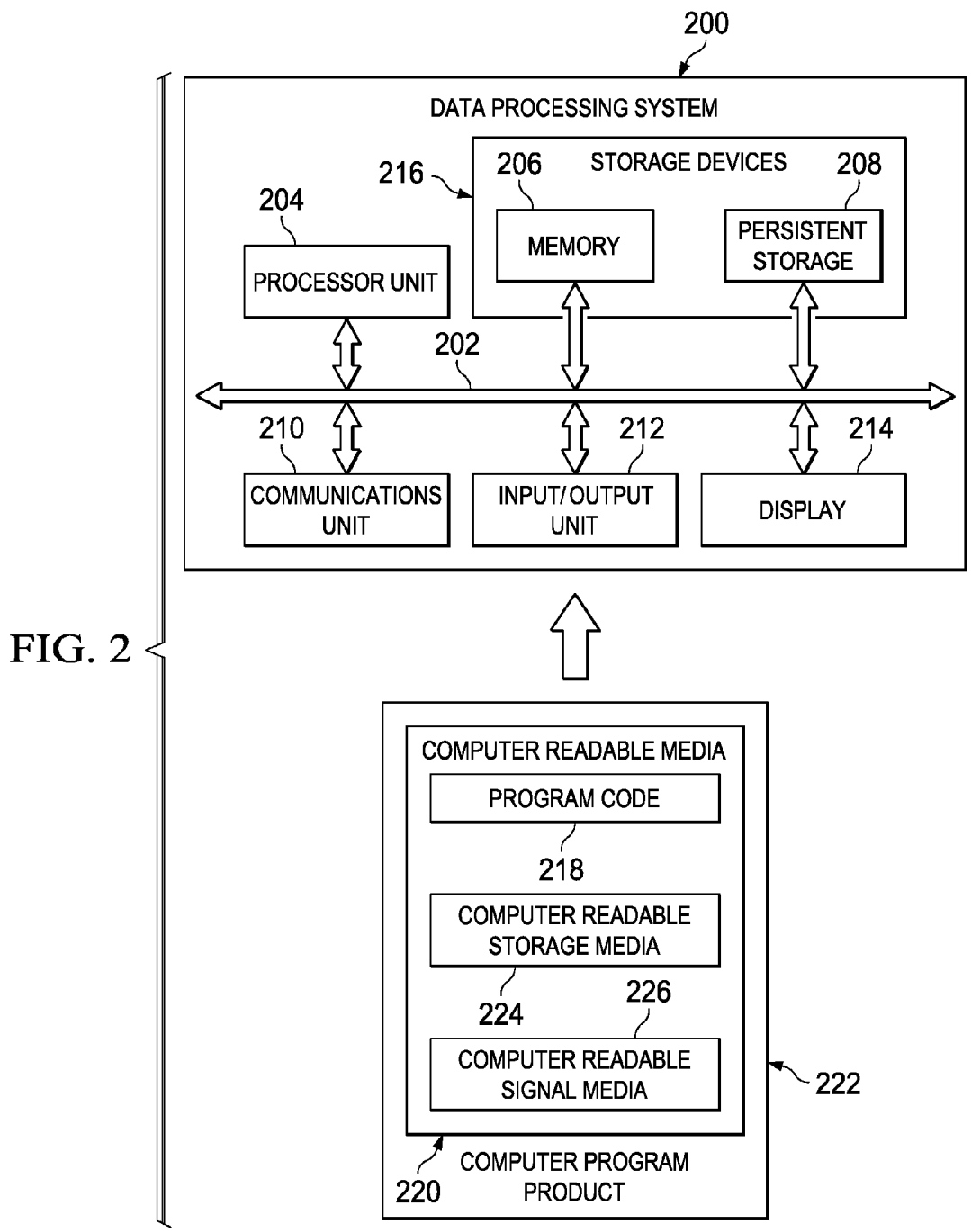
FIG. 2 is a block diagram of a data processing system in accordance with an illustrative embodiment.

Processor unit 304 may be, for example, an illustrative example of one implementation of processor unit 204 of data processing system 200 in FIG. 2, or some other device that may execute processes to control chemical dispersion by number of chemical dispersion nodes 300. Processor unit 304 may be connected to the different components and systems of chemical dispersion node 302, such as number of sensors 308, communications unit 306, and cartridge 312. As used herein, "connected to" refers to the processor unit being in communication with the different components and systems of chemical dispersion node 302 in a manner such that information can be exchanged between processor unit 304 and the different components and systems of chemical dispersion node 302. In an illustrative example, information may be anything that can be sent between the components and systems of chemical dispersion node 302 to control chemical dispersion by the node and/or sensor data collection by the node. Examples of information include, but are not limited to, data, commands, programs, signals, and/or any other suitable information.

Processor unit 304 may send various commands to these components to operate chemical dispersion node in different modes of operation, such as data collection and chemical dispersion modes, for example. These commands may take various forms depending on the implementation. For example, the commands may be analog electrical signals in which a voltage and/or current change is used to control these systems. In other implementations, the commands may take the form of data sent to the systems to initiate the desired actions. Processor unit 304 may be a single processing unit, two processing units, or distributed across a number of processing units. As used herein, a number refers to one or more processing units.

Communications unit 306 is a communications system that provides communications links and channels to processor 304 to send and/or receive information. In one illustrative example, the communication links and channels may be heterogeneous and/or homogeneous redundant components that provide fail-safe communication. This information includes, for example, data, commands, and/or instructions.

Communications unit 306 may take various forms. For example, communications unit 306 may include a wireless communications system, such as a cellular phone system, a Wi-Fi wireless system, a Bluetooth wireless system, and/or some other suitable wireless communications system. Further, communications unit 306 also may include a communications port, such as, for example, a universal serial bus port, a serial interface, a parallel port interface, a network interface, and/or some other suitable port to provide a physical communications link. Communications unit 306 may be used to communicate with a remote location, such as remote location 104 in FIG. 1, or an operator, such as user 112 in FIG. 1.

Number of sensors 308 may be a set of sensors used to collect information about the environment around a chemical dispersion node. In these examples, the information is sent to processor unit 304 to provide data in identifying how chemical dispersion node 302 should manage chemical dispersion for pest problem resolution, specifically providing data about the pests and current conditions in the operating environment. In these examples, "a set" refers to one or more items. A set of sensors is one or more sensors in these examples.

Power source 310 may be any suitable type of device for providing power to number of sensors 308 and processor unit 304. Power source 310 may include, in some illustrative examples, energy harvester 314 and energy storage 316. Energy harvester 314 may be, for example, without limitation, solar cells, wind turbines, piezo electric vibration elements, and/or any other suitable energy harvester. Energy storage 316 may be, for example, without limitation, a battery, a capacitor, or a fuel cell. In one illustrative example, energy storage 316 may be recharged by energy harvester 314.

Cartridge 312 is an example of one type of dispersion system that may be located on chemical dispersion node 302 for executing a pest resolution, such as applying chemicals to treat an identified pest problem. Cartridge 312 enables chemical dispersion node 302 to apply a resource, such as a chemical, to an area, such as area 116 in FIG. 1. Cartridge 312 includes disperser 318 and reservoir 320. Disperser 318 may be any type of component or device configured to apply a resource to an area. Disperser 318 may include, for example, without limitation, a hose, nozzle, pump, sprayer, tubing, wiper, cloth, roller, laser, electromagnetic wave generator, light emitter, sound generator, electrical pulse generator, mister, fogger, duster, atomizer, gas stream, mechanical finger, heating element, and/or any other suitable disperser.

In one exemplary embodiment, a chemical is dispensed into the air. Diffusion, wind or other air movement causes the chemical to be spread in the air associated with the area. The chemical may be sensed by another node, confirming the chemical has been dispersed in the area between the two nodes. This observation may be reported to other chemical dispersion nodes or the remote location. An analogous example exists if the chemical is dispersed into and transported in surface water.

Reservoir 320 is an illustrative example of a type of chemical storage system used by chemical dispersion node 302. Reservoir 320 includes chemical 322 and level 324. Level 324 monitors the amount of chemical 322 in reservoir 320 and the amount of chemical 322 applied at a particular location. Chemical 322 may be any type of chemical suitable for addressing a pest problem. Chemical 322 may include, for example, without limitation, DEET, citronella, essential oils, scents, fragrances, picaridin, nepetelactone, permethrin, neem oil, Bog Myrtle, herbicides, and/or any other suitable chemical.

In an illustrative embodiment, level 324 may be, for example, a float in reservoir 320. The vertical position of the float may be representative of the amount of chemical 322 in reservoir 320. In an illustrative embodiment, the float may be a sensor that tracks the change of chemical levels over time, and transmits the sensor data to a processing system, such as processor unit 304. In another illustrative embodiment, level 324 may be a device for measuring the flow rate of chemical 322 as chemical 322 passes from reservoir 320 through disperser 318.

The amount of a chemical to be applied to an area is specified by chemical dispersion plan received from a remote location, such as remote location 104 in FIG. 1.

The illustration of number of chemical dispersion nodes 300 in FIG. 3 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

For example, in some illustrative embodiment, number of chemical dispersion nodes 300 may contain additional systems in place of or in addition to the systems depicted. In other illustrative embodiments, each cartridge may include one or more partitioned reservoirs containing one or more resources or chemicals. The resources or chemicals within the one or more partitioned reservoirs of a cartridge may be homogenous and/or heterogeneous, for example. Cartridges may be permanently integrated in the chemical dispersion node, be removable, or have components which are individually replaceable.

Figure 4:
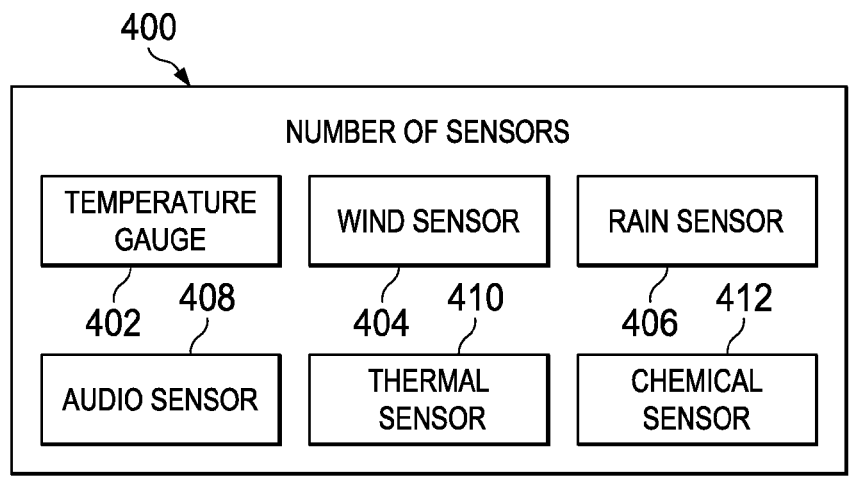
FIG. 4 is a block diagram of a number of sensors in accordance with an illustrative embodiment.

With reference now to FIG. 4, a block diagram of a number of sensors is depicted in accordance with an illustrative embodiment. Number of sensors 400 is an illustrative example of one implementation of number of sensors 308 in FIG. 3.

As illustrated, number of sensors 400 includes, for example, temperature gauge 402, wind sensor 404, rain sensor 406, audio sensor 408, thermal sensor 410, and chemical sensor 412. These different sensors may be used to identify pest problems and/or current conditions in an operating environment around a chemical dispersion node.

Temperature gauge 402 detects the ambient temperature of the operating environment. Wind sensor 404 detects the wind speed in an operating environment. Rain sensor 406 detects precipitation on an exterior surface of the chemical dispersion node. In one embodiment, rain sensor 406 includes an infrared beam and an infrared sensor. In this illustrative example, rain sensor 406 operates by beaming an infrared light at a 45-degree angle into a clear glass or plastic component of the chemical dispersion node from the inside of the chemical dispersion node. If the clear glass or plastic component is wet, less light makes it back to the sensor, indicating the presence of moisture on the component and the likelihood of rain. The illustrative embodiment is not meant to limit the architecture of rain sensor 406. Other rain detection technologies may be used without departing from the spirit and scope of the invention.

Audio sensor 408 is any type of device for detecting sound and converting it into an electrical signal for processing, such as by processor unit 304 in FIG. 3. Audio sensor 408 may be, for example, without limitation, a microphone.

Thermal sensor 410 detects heat temperature from living organisms, such as animals and humans, when the living organism is in a certain proximity to thermal sensor 410. Chemical sensor 412 detects saturation or concentration of chemicals in the operating environment around a chemical dispersion node. Chemical sensor 412 may also be used to determine the amount of chemical dispersed by a node, for example.

The illustration of number of sensors 400 in FIG. 4 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

For example, in some illustrative embodiments, additional sensors may be implemented in number of sensors 400.

Figure 5:
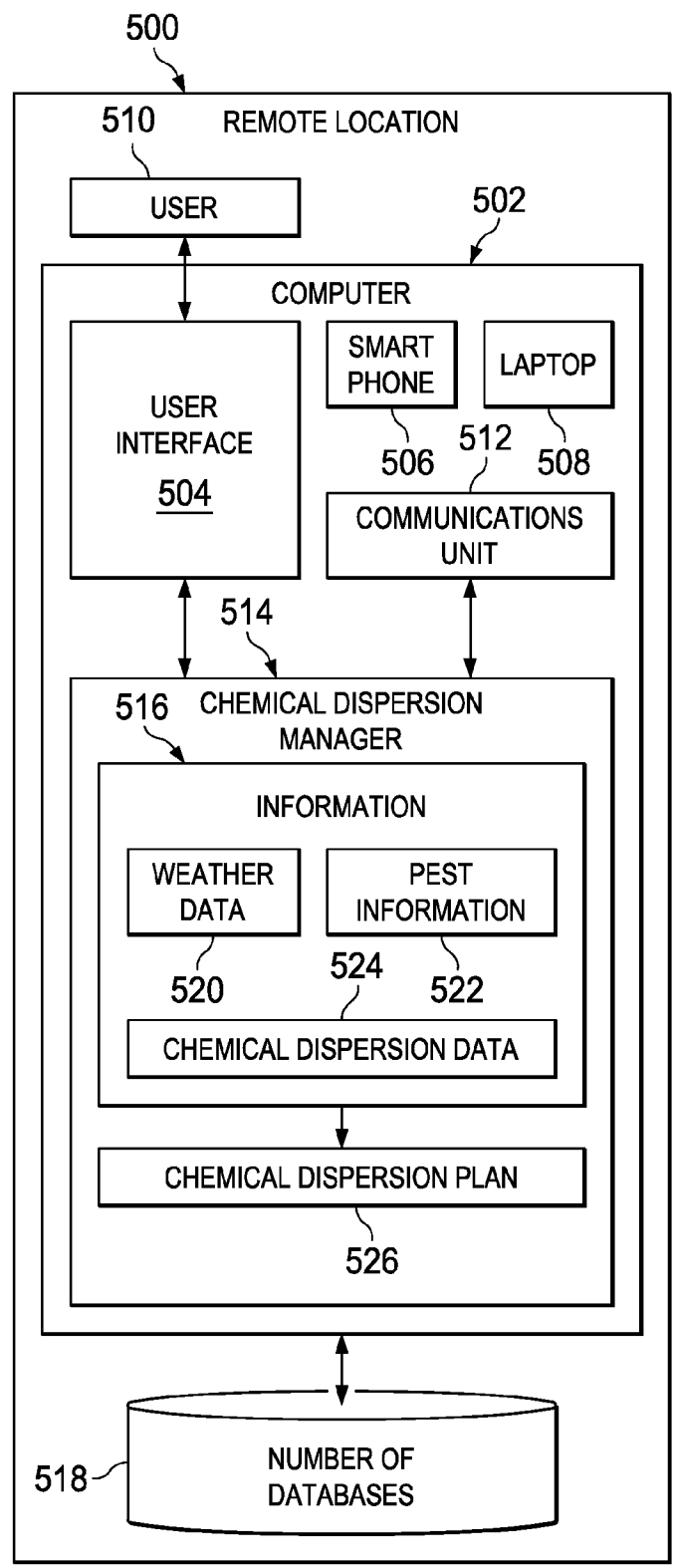
FIG. 5 is a block diagram of a remote location in accordance with an illustrative embodiment.

With reference now to FIG. 5, a block diagram of a remote location is depicted in accordance with an illustrative embodiment. Remote location 500 is an illustrative example of one implementation of remote location 104 in FIG. 1.

Remote location 500 includes computer 502. Computer 502 is an illustrative example of one implementation of data processing system 200 in FIG. 2. Computer 502 includes user interface 504. In one illustrative example, computer 502 may be implemented as smart phone 506. In another illustrative example, computer 502 may be implemented as laptop 508. User 510 may interact with computer 502 using user interface 504.

User interface 504 may be, in one illustrative embodiment, presented on a display monitor integrated with and/or connected to computer 502 and viewable by user 510. User interface 504 may provide a means for user 510 to initiate a chemical dispersion task and/or provide user input regarding an area of interest for pest control management.

Computer 502 also includes communications unit 512 and chemical dispersion manager 514. Communications unit 512 is an illustrative example of communications unit 210 in FIG. 2. Chemical dispersion manager 514 may be a processor unit, such as processor unit 204 in FIG. 2.

Chemical dispersion manager 514 may be implemented by a processor unit, such as processor unit 204 in FIG. 2. Chemical dispersion manager 514 receives a trigger to generate a chemical dispersion plan and retrieves information 516. The trigger may be received from a user, such as user 510, using user interface 504 to initiate resolution of a pest problem, in one illustrative example. In another illustrative example, the trigger may be a scheduled event stored in number of databases 518.

Information 516 may be collected from number of databases 518 for the area associated with a number of chemical dispersion nodes, such as number of chemical dispersion nodes 300 in FIG. 3. Information 516 may include weather data 520, pest information 522, and chemical dispersion data 524. Weather data 520 may be forecasted or reported weather retrieved from a weather source, or current weather data for the operating environment around a number of chemical dispersion nodes collected by a number of sensors associated with the nodes.

Pest information 522 may be data collected by a number of sensors associated with a number of chemical dispersion nodes and/or data input from a user, such as user 510. In an illustrative example, user 510 may input pest information 522 indicating a mosquito problem for a given area that requires treatment.

Chemical dispersion data 524 may be information about past chemical dispersion in the area selected for treatment. Chemical dispersion data 524 may be used by chemical dispersion manager 514 to determine the amount of chemical to disperse in an upcoming treatment, based on safety levels, regulatory levels, and/or any other factors associated with the area for treatment.

Chemical dispersion manager 514 uses information 516 to generate chemical dispersion plan 526. Chemical dispersions plan 526 is a chemical application plan for a given area to treat a given pest problem. Chemical dispersion plan 526 may detail an amount of a chemical to disperse, a type of dispersion for the chemical, an area for dispersion of the chemical, a time for dispersion of the chemical, and/or any other chemical dispersion guidelines. Chemical dispersion manager 514 sends chemical dispersion plan 526 to a number of chemical dispersion nodes using communications unit 512.

The illustration of remote location 500 in FIG. 5 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

Figure 6:
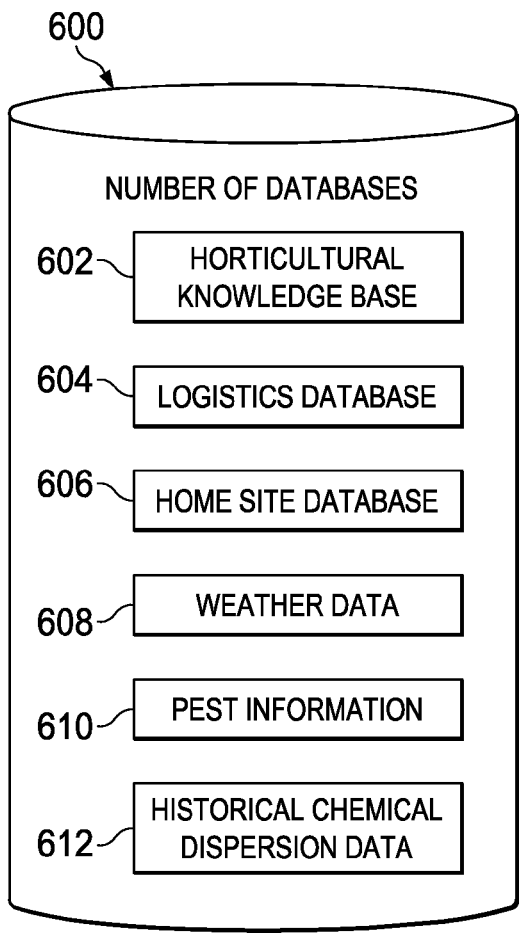
FIG. 6 is a block diagram of a number of databases in accordance with an illustrative embodiment.

With reference now to FIG. 6, a block diagram of a number of databases is depicted in accordance with an illustrative embodiment. Number of databases 600 may be located in a remote location, such as remote location 104 in FIG. 1 and/or remote location 500 in FIG. 5, or distributed across both a remote location and a number of chemical dispersion nodes.

Number of databases 600 may include horticultural knowledge base 602, logistics database 604, home site database 606, weather data 608, pest information 610, and historical chemical dispersion data 612.

Horticultural knowledge base 602 contains information about an operating environment, such as, for example, a fixed map showing the landscape, structures, tree locations, flowerbed locations, individual plant locations, and other static object locations. Horticultural knowledge base 602 may also contain information, such as, without limitation, plant species and varieties located in the operating environment, information about the water needs, growth stages, and life cycles of the plant species and varieties located in the operating environment, current weather for the operating environment, weather history for the operating environment, pest and insect species native to and/or common to the operating environment, and/or any other suitable information for management and execution of pest problem management and resolution. The information in horticultural knowledge base 602 may be used to perform classification, identify problems and/or pests, and plan actions for pest problem management.

Logistics database 604 includes information about the chemicals, chemical application types, chemical application amounts associated with different pest problems, and cost of addressing different pest problems.

Home site database 606 contains information specific to a given area or location. The information in home site database 606 may be defined by an owner of the given area or location, for example, such as a home owner or property manager. Home site database 606 may be associated with area 116 in FIG. 1, for example. Home site database 606 includes local area weather, area schedule, area inhabitants, environmental impacts, area budget, area brands, and available applicators. Area weather may include information about the current weather for an area and/or weather forecasts for the area.

Area schedule contains information about scheduled events and/or use of an area. In an illustrative example, an area schedule may include, without limitation, dates and times when the area is occupied, dates and times when the area is unoccupied, dates and times when the area is occupied by humans, dates and times when the area is occupied by pets, dates and times when the area is occupied by children, dates and times when resource application is prohibited, dates and times when resource application is preferred, and the like.

Area inhabitants contain information about the anticipated or expected human and/or animal inhabitants of an area. For example, area inhabitants may contain information about the type of pets who frequent the area, such as cats or dogs. Environmental impacts contain information about the environmental impact to the area associated with a given chemical application.

Area budget contains information about the pre-defined monetary expenditure constraints placed on chemical application to an area. For example, area budget may include a monthly budgetary allotment that a treatment plan must fall within to be acceptable for application to the area. Area brands contains information about pre-defined product brands, preferred applicators, chemical handling guidelines, and other parameters defined by an owner for treatment plans to the area.

Available applicators contain information about the application means available to an area. Available applicators may include, for example, without limitation, a number of chemical dispersion nodes.

Weather data 608 may be a separate database of weather information than that of home site database 606. Weather data 608 may be, for example, weather information for a given area retrieved from an outside weather source. Pest information 610 may contain information about the pests associated with an area, a geographic location, a season, and past pest information for a given area. Historical chemical dispersion data 612 may contain a record of past chemical dispersion treatments addressing pest problems and the results. For example, the amount of a chemical applied and the last time it was applied may be used by a chemical dispersion system to determine what a safe amount and time for a next chemical dispersion may be, for example.

Figure 7:
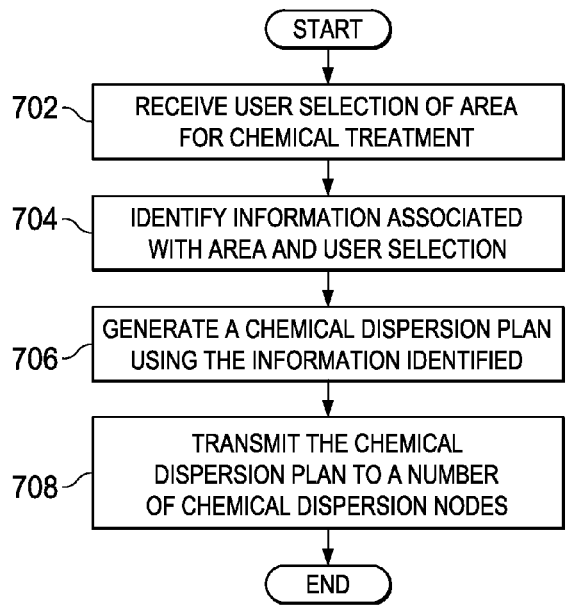
FIG. 7 is a flowchart illustrating a process for networked chemical dispersion in accordance with an illustrative embodiment.

With reference now to FIG. 7, a flowchart illustrating a process for networked chemical dispersion is depicted in accordance with an illustrative embodiment. The process in FIG. 7 may be implemented by networked chemical dispersion system 100 in FIG. 1, for example.

The process begins by receiving a user selection of an area for chemical treatment (step 702). The area may be, for example, a backyard patio of a residential dwelling. The user selection may include details about the type of undesired pests for the area, a desired time for pest treatment, and/or a desired time for use of the area by the user. In another illustrative example, the type of pests to treat may be pre-configured by the user at an earlier time, and the user selection may simply include a selection of an area for treatment and a time at which the user desires to enjoy the area free from pests.

Next, the process identifies information associated with the area and the user selection (step 704). The information may be retrieved using a plurality of databases, such as plurality of databases 600 in FIG. 6, by a chemical dispersion manager, such as chemical dispersion manager 514 in FIG. 5. The process then generates a chemical dispersion plan using the information identified (step 706). The chemical dispersion plan may include a type of chemical to disperse, a time for dispersions, a type of dispersion technique, and the given area in which to disperse the chemical.

The process transmits the chemical dispersion plan to a number of chemical dispersion nodes (step 708), with the process terminating thereafter. The number of chemical dispersion nodes receives the plan and execute the plan accordingly.

Figure 8:
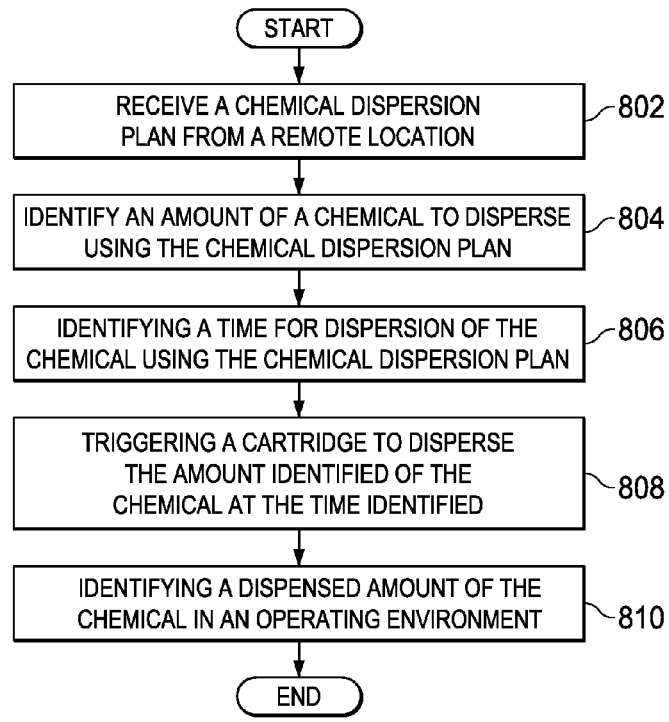
FIG. 8 is a flowchart illustrating a process for executing a chemical dispersion plan in accordance with an illustrative embodiment.

With reference now to FIG. 8, a flowchart illustrating a process for executing a chemical dispersion plan is depicted in accordance with an illustrative embodiment. The process in FIG. 8 may be implemented by a component such as chemical dispersion node 302 in FIG. 3, for example.

The process begins by receiving a chemical dispersion plan from a remote location (operation 802). The chemical dispersion plan may be generated at the remote location in response to a trigger, such as a user selection of an area for chemical treatment, for example.

The process identifies an amount of a chemical to disperse using the chemical dispersion plan (operation 804). The chemical dispersion plan may include a number of different parameters for chemical dispersion, such as a type of chemical to disperse, an amount of chemical to disperse, a time at which to disperse the chemical, an area at which to disperse the chemical, and so on. The process also identifies a time for dispersion of the chemical using the chemical dispersion plan (operation 806).

The process then triggers a cartridge to disperse the amount identified of the chemical at the time identified (operation 808). The cartridge may be part of a chemical dispersion node, such as chemical dispersion node 302 in FIG. 3, having a disperser and a chemical in a reservoir, for example. The process identifies a dispensed amount of the chemical in an operating environment (operation 810), with the process terminating thereafter.

The identification of the dispensed amount may be an identification made using a sensor system of a chemical dispersion node, for example. In one illustrative embodiment, the chemical dispersion node dispensing the chemical in response to the chemical dispersion plan may use a sensor system to monitor the disbursement of the chemical into the operating environment. In another illustrative embodiment, the chemical dispersion node identifying the dispensed amount may be a node other than the number of nodes that dispensed the chemical. The chemical dispersion node sensing or identifying the dispensed amount may transmit the dispersed amount data to the remote location, in an illustrative example.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The illustrative embodiments recognize a need for a networked means of dealing with pest problems, which reduces the human labor required to address the problems and reduces chemical handling and storage.

The different illustrative embodiments recognize and take into account that identifying and treating problems is currently a labor intensive task. When a pest problem is noticed by a home owner, for example, the home owner typically engages in various manual applications of chemicals to attempt to eradicate the problem. Alternately, the home owner may hire third party to apply chemicals around a yard or home. The home owner must then monitor the results and determine when future applications are necessary. This implementation may involve contacting a professional lawn or gardening service, making a trip to a retailer for supplies, ordering chemicals, studying chemical application, performing the chemical application, cleaning up after the application, and then storing any unused chemicals. This current approach is time consuming and often results in leftover chemicals being stored and presenting potential safety hazards.

Therefore, the illustrative embodiments provide networked chemical dispersion system that identifies pest problems, determines treatment plans, and applies the treatment to the area with the problem in order to resolve the issue detected.

The description of the different advantageous embodiments has been presented for purposes of illustration and description, and is not intended to be exhaustive or limited to the embodiments in the form disclosed. Many modifications and variations will be apparent to those of ordinary skill in the art. Further, different embodiments may provide different advantages as compared to other embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for networked chemical dispersion, the method comprising:
   receiving a user selection of an area for chemical treatment;
   identifying information associated with the area and the user selection;
   generating a chemical dispersion plan using the information identified; and
   transmitting the chemical dispersion plan across a network to a number of remote chemical dispersion nodes, wherein the number of remote chemical dispersion nodes execute the chemical dispersion plan using a processor unit that executes the chemical dispersion plan and a disperser that disperses a chemical.

2. The method of claim 1, wherein the disperser is selected from at least one of a hose, nozzle, pump, sprayer, tubing, wiper, cloth, roller, laser, electromagnetic wave generator, light emitter, sound generator, electrical pulse generator, mister, fogger, duster, atomizer, gas stream, mechanical finger, and heating element.

3. A method for executing a chemical dispersion plan, the method comprising:
   receiving, by a processor unit, a chemical dispersion plan from a remote location using a communications unit;
   identifying an amount of a chemical to disperse using the chemical dispersion plan;
   identifying a time for dispersion of the chemical using the chemical dispersion plan; and
   triggering a cartridge to disperse the amount identified of the chemical at the time identified, wherein the processor unit, the communications unit, and the cartridge are part of a chemical dispersion node that receives and executes the chemical dispersion plan.

4. A method for executing a chemical dispersion plan, the method comprising:
   receiving, by a processor unit, a chemical dispersion plan from a remote location using a communications unit;
   identifying an amount of a chemical to disperse using the chemical dispersion plan;
   identifying a time for dispersion of the chemical using the chemical dispersion plan; and
   triggering a cartridge to disperse the amount identified of the chemical at the time identified; and
   identifying a dispensed amount of the chemical dispensed in an operating environment by the chemical dispersion node, wherein the chemical is dispensed by a number of chemical dispersion nodes other than a chemical dispersion node identifying the dispensed amount of the chemical, and wherein the chemical dispersion node identifying the dispensed amount transmits the dispensed amount identified to the remote location.

5. A method for executing a chemical dispersion plan, the method comprising:
   receiving, by a processor unit, a chemical dispersion plan from a remote location using a communications unit;
   identifying an amount of a chemical to disperse using the chemical dispersion plan;
   identifying a time for dispersion of the chemical using the chemical dispersion plan; and
   triggering a cartridge to disperse the amount identified of the chemical at the time identified;
   identifying a dispensed amount of the chemical dispensed in an operating environment by the chemical dispersion node; and
   transmitting the dispensed amount to the remote location using the communications unit.

6. A method for networked chemical dispersion, the method comprising:

receiving a user selection of an area for chemical treatment;

identifying information associated with the area and the user selection;

generating a chemical dispersion plan using the information identified;

transmitting the chemical dispersion plan across a network to a number of remote chemical dispersion nodes;

receiving, by a processor unit of a given one of the number of chemical dispersion nodes, the chemical dispersion plan from a remote location using a communications unit; and executing, by the processor unit, the chemical dispersion plan that specifies an amount of chemical to be applied to the area.

7. A method for networked chemical dispersion, the method comprising:

receiving a user selection of an area for chemical treatment;

identifying information associated with the area and the user selection;

generating a chemical dispersion plan using the information identified;

transmitting the chemical dispersion plan across a network to a number of remote chemical dispersion nodes; and receiving the information associated with the area from at least one of the number of chemical dispersion nodes, wherein the information associated with the area is retrieved from at least one database associated with the number of chemical dispersion nodes.

8. A method for networked chemical dispersion, the method comprising:

receiving a user selection of an area for chemical treatment at a first location;

identifying information associated with the area and the user selection at the first location;

generating a chemical dispersion plan using the information identified at the first location;

transmitting the chemical dispersion plan across a network to a number of chemical dispersion nodes located remotely from the first location;

receiving, by a processor unit of a given one of the number of chemical dispersion nodes, the chemical dispersion plan from the first location using a communications unit;

identifying an amount of a chemical to disperse using the chemical dispersion plan by the given one of the number of chemical dispersion nodes;

identifying a time for dispersion of the chemical using the chemical dispersion plan by the given one of the number of chemical dispersion nodes; and triggering a cartridge to disperse the amount identified of the chemical at the time identified by the given one of the number of chemical dispersion nodes.

* * * * *